United States Patent [19]

Honda

[11] Patent Number: 4,633,307

[45] Date of Patent: Dec. 30, 1986

[54] DIGITAL SUBTRACTION FLUOROGRAPHIC METHOD AND APPARATUS

[75] Inventor: Michitaka Honda, Nishinasunomachi, Japan

[73] Assignee: Kabushiki Kaisha Toshiba, Kawasaki, Japan

[21] Appl. No.: 772,861

[22] Filed: Sep. 5, 1985

[30] Foreign Application Priority Data

Sep. 13, 1984 [JP] Japan .................................. 59-190700

[51] Int. Cl.⁴ .......................... H05G 1/64; H04N 5/32
[52] U.S. Cl. ....................................... 358/111; 378/99
[58] Field of Search .................. 378/99, 901; 358/111, 358/110

[56] References Cited

U.S. PATENT DOCUMENTS

| | | | |
|---|---|---|---|
| 4,204,225 | 5/1980 | Mistretta | 378/99 |
| 4,204,226 | 5/1980 | Mistretta et al. | 378/99 |
| 4,436,095 | 3/1984 | Kruger | 358/111 |
| 4,504,908 | 3/1985 | Riederer et al. | 358/111 |
| 4,542,459 | 9/1985 | Riederer | 378/99 |

Primary Examiner—Craig E. Church
Assistant Examiner—Charles Wieland
Attorney, Agent, or Firm—Oblon, Fisher, Spivak, McClelland, & Maier

[57] ABSTRACT

In a digital intravenous subtraction fluorographic system, X-ray subtraction images obtained by performing a subtraction between the precontrast images and the post-contrast images are processed by comparing, for each pixel, the value of the pixel image data in the difference image with a predetermined threshold intensity value, and recognizing the time until the value of the pixel image data reaches the threshold intensity value. The resulting time data so determined in the processor is used for displaying the distribution of contrast medium in the vessel in relation to the time periods it takes for each pixel to attain the predetermined threshold intensity. In effect, the time data for each pixel is itself converted to an intensity signal dependent on the amount of time it takes for each pixel to cross the predetermined threshold intensity, and it is the time period derived intensity signal which is displayed.

4 Claims, 11 Drawing Figures

DIGITAL SUBTRACTION FLUOROGRAPHIC METHOD AND APPARATUS

BACKGROUND OF THE INVENTION

1. Field of the Invention

The present invention relates in general to digital subtraction fluorography, and more particularly concerns a method and apparatus for use in connection with temporal subtraction of X-ray images with phase information.

2. Discussion of the Background

Digital subtraction fluorographic apparata and methods have previously been used for visualizing the flow of an X-ray contrast medium through blood vessels. One digital fluorography technique involves projecting an X-ray beam through a body, converting the resulting X-ray image to an optical image with an image intensifier, converting the optical image to analog video signals with a video camera and then digitizing the video signals to form a matrix of digital values that correspond in magnitude to the intensity of the picture elements (pixels) that compose the image. In temporal imaging, an image of a region of the anatomy that contains the blood vessels of interest is obtained before an intravenously injected X-ray opaque medium reaches the vessels. This image is typically stored as a mask image. When the X-ray contrast medium begins to flow through the vessels, a series of live images are obtained. The mask image is then subtracted from the successive live images to produce a sequence of difference images. The object of the subtraction is to cancel all unchanged image content such as from bone and soft tissue in the mask and live images so that only the image of the contrast medium containing blood vessels remains for display.

In the art known to applicant, the data for one or both or even more images in succession are usually weighted or otherwise operated on to bring about cancellation of obscuring background and to have the anatomy of interest remain. However, such techniques neither recognize nor take into account that the concentration of contrast medium in the vessel as a function of time. Phase information contained in the difference image at any moment in time is ignored, and not utilized for diagnosis purposes.

One method assuming that the concentration of contrast medium in the blood vessels varies with time is to plot concentration for each pixel in the selected region of interest versus time. A plot of concentration versus time results in a curve representing the blood flow in the blood vessels of interest. However, the prior method is characterized by the following disadvantages:

(a) it is impossible to provide phase information contained in the blood flow over the whole of the blood vessels of interest;

(b) it is impossible to measure the concentration of contrast medium which varies with time, in the selected portion of the blood vessels of interest; and (c) it is impossible to superimpose the outline of the blood vessels defined by the blood flow containing the X-ray contrast medium and the phase information arising from the blood flow in the blood vessels.

In other words, an X-ray contrast medium is not being observed as it flows through the blood vessels, and the only contrast difference between successive X-ray images, which is due to the leading edge of the contrast medium having advanced during the integrating interval, is displayed.

SUMMARY OF THE INVENTION

Accordingly, an object of the present invention is to provide a novel method and apparatus that enables display of subtracted images of an anatomical object through which blood flows, which display is representative of a distribution of contrast medium varying with time wherein there is a relatively low concentration of contrast medium when the medium first reaches a peak concentration followed by a decline until the vessel is again occupied by blood that does not contain any contrast medium.

The above object, as well as others, is achieved according to the invention by providing a novel method and apparatus by which phase difference images of blood vessels are displayed. According to the invention, there is derived a signal corresponding to the difference in time after the contrast medium reaches each pixel defined by the blood vessels of interest and upon the pixel reaching a predetermined concentration. This difference signal is used for displaying the phase difference image of the blood vessels on a television monitor.

In obtaining the signal representative of the time difference in the contrast medium having advanced through the blood vessels, the corresponding pixel data which represent the intensities of the picture elements (pixels) that compose the subtracted image derived by successive subtracting of a subsequent live image from the mask image are compared with predetermined reference data to measure the time that the blood containing the contrast medium has advanced through the blood vessels.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
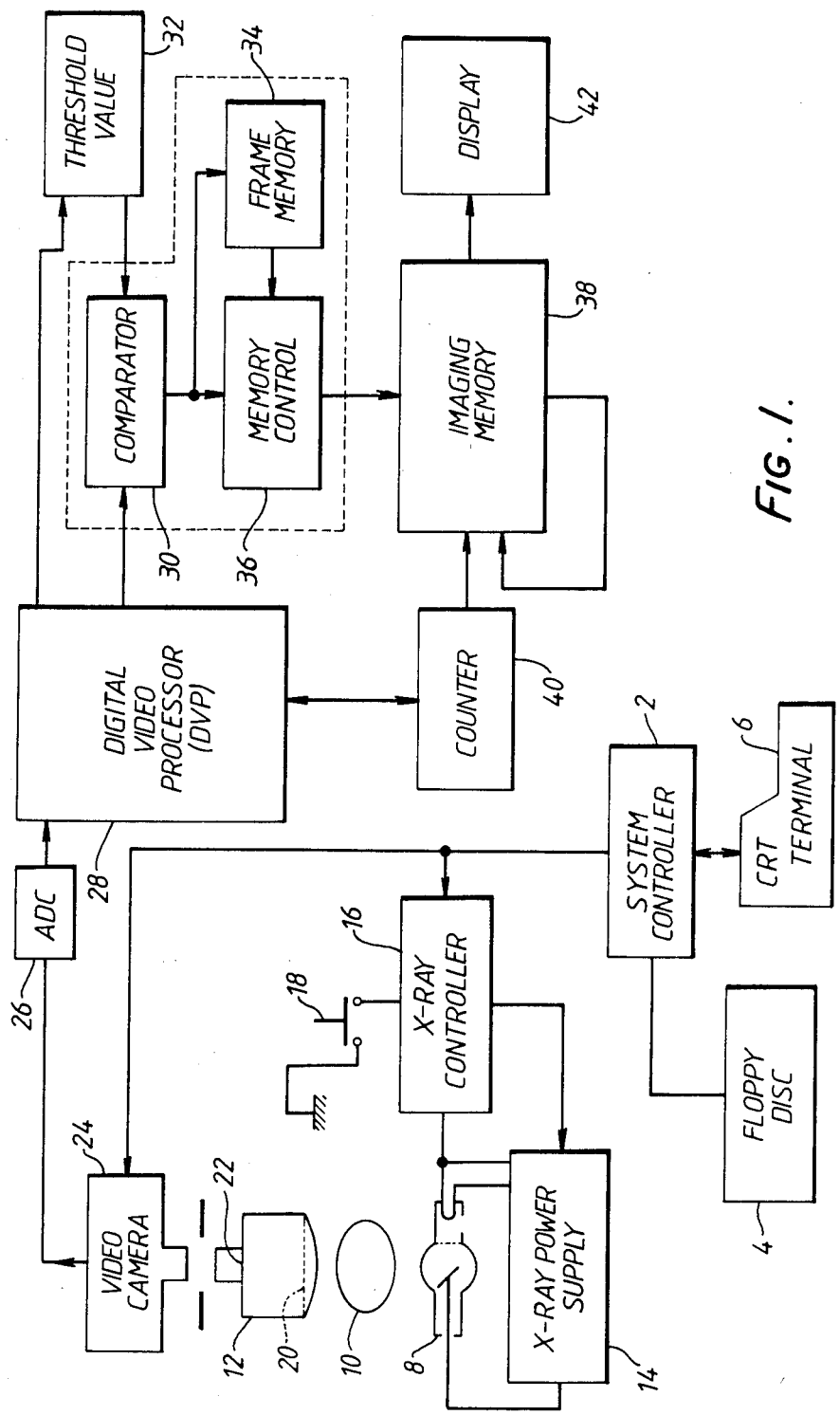
FIG. 1 is a block diagram of the essential components of an apparatus for acquiring data for phase difference images of blood flow, processing the data in accordance with the invention, and displaying a resulting image.

Referring now more specifically to FIG. 1, there is shown a system for producing the pixel data for phase difference images of blood vessels. The host CPU system controller is represented by the block marked 2. Its software may be stored on floppy disk which is symbolized by block 4. A CRT terminal 6 is the user interface for communicating with the system. In accordance with the invention, if the radiologist user desires to perform a particular fluorographic procedure, the user need only feed the identification for the procedure by way of the CRT terminal 6 keyboard to the CPU 2. For the present, by way of example, the user may want to perform a procedure where a mask image is obtained followed by an image or series of images wherein an X-ray contrast medium in the blood vessels appears in the view and the latter image or images have the mask image subtracted therefrom.

For the purposes of the subtraction method described herein, an X-ray tube 8 is energized to project a high photon energy and low intensity beam through the patient 10 interposed between the X-ray tube 8 and an X-ray image intensifier 12. The X-ray tube 8 is energized from a power supply 14. The X-ray power supply is controlled with conventional control circuitry 16. The X-ray control circuitry is designed to provide X-ray beams of approximate energy and intensity by control instructions received from CPU 2, which instructions have been formatted by CPU 2 in response to user commands entered via CRT terminal 6. X-ray exposure sequences may be initiated by the traditional foot switch or hand switch 18. Closing switch 18 may initiate an X-ray exposure sequence provided from CPU 2.

Whenever X-ray source 8 is energized, it projects a beam through patient 10 to produce an X-ray image which is received on a photocathode screen 20 in the X-ray image intensifier tube 12. Photocathode screen 20 converts the X-ray image to an electron image which is focused to produce a corresponding bright and magnified optical image on the output phosphor 22 of the intensifier. The optical version of the X-ray image is viewed with a television or video camera 24. When the target of the tube in video camera 24 is scanned, an analog video waveform is output to an analog-to-digital converter (ADC) 26. ADC 26 samples the analog video waveform and converts it to digital values corresponding in magnitude to the intensities of the picture elements (pixels) that compose the X-ray image. These digital values are conducted to the input of a processing circuit, which, for convenience, is called a digital video processor (DVP) and is represented by the block marked 28. DVP 28 is a versatile device that can operate on and manipulate data in various ways.

More particularly, DVP 28 has at least two full video frame memories configured such that continuous video frames can be integrated into either or both memories. The DVP 28 also has digital circuitry capable of subtracting the contents of one memory from either that of the other memory or from the live incoming video signal and additional circuitry to add a gain and offset to the resultant difference image.

Figure 2:
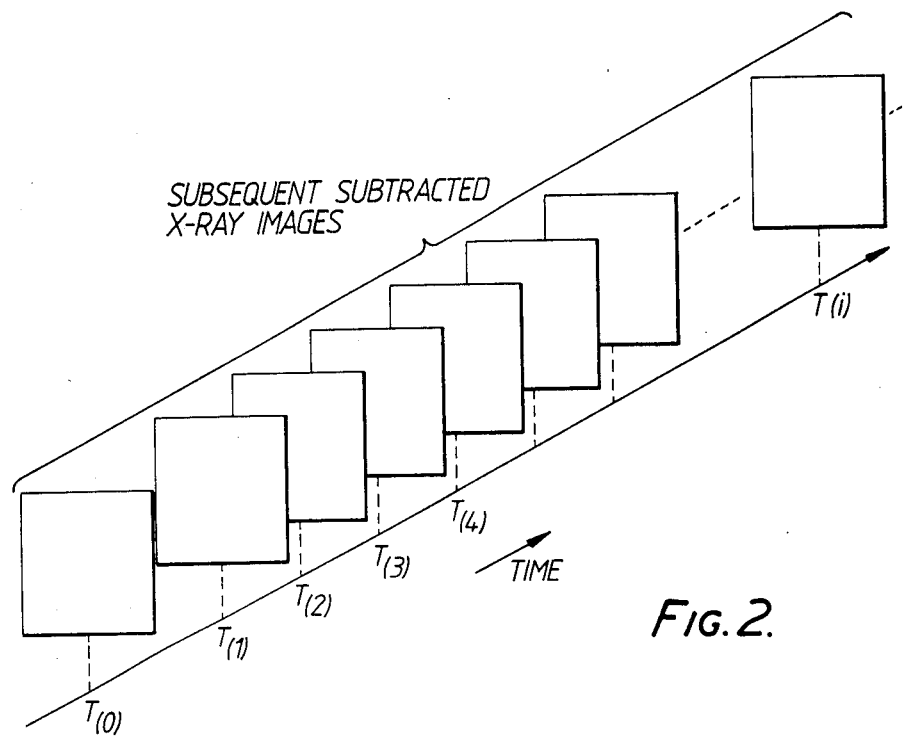
FIG. 2 is a schematic illustration of the acquisition of consecutive contrast images according to the invention.

The most common practice before development of the system shown in FIG. 1 was to pulse the X-ray tube on and off and to read out the video camera and convert the video signal therefrom to digital picture element (pixel) intensity values between exposures. As is known, for image subtraction, a sequence of one or more mask images are made of the region of the anatomy that contains the blood vessels of interest. The mask images are made before an X-ray contrast medium arrives in the region of interest. Generally, the contrast medium arrives in the region of interest anywhere up to about 20 seconds after it has been injected. The imaging sequence is continued after the contrast medium enters the vessels in the region of interest and possibly for a short time after it has left and has been replaced by blood that does not contain any contrast medium. Thus, as shown in FIG. 2, a sequence of television frames containing pre-contrast images are obtained at time T(0), T(1) . . . followed by contrast images obtained at, e.g., T(4), T(5) . . ., etc. followed by post-contrast images which are obtained at T(i−1), T(i).

Referring again to FIG. 1, the digital data which correspond to the intensities of pixels that compose the resultant difference image is output from DVP 28 to a comparator 30 wherein the digital pixel signals are compared with a threshold value provided from a threshold value TH introducing device 32. The resultant signal of comparison in the comparator 30 is conducted to both a frame memory 34 for temporary storing of the output of the comparator 30 and a memory controller 36. Controller 36 enables an imaging memory 38 to receive the output of a counter 40 which represents the time period during which the projected intensity of the contrast medium in the blood vessels of interest reaches the threshold value TH as will be described in detail hereinafter.

The threshold level TH from the device 32 is set at a value which falls within an arbitrary range around the half-maximum point on the concentration curve wherein there is a relatively low concentration of contrast medium when the medium first reaches the blood vessels of interest and then it reaches a peak concentration followed by a decline until the contrast medium is substantially out of the region of interest. Further, the threshold value TH is determined so as to exceed the noise in the subtracted images which is accumulated during successive subtraction between the mask and the line images.

Therefore, the digital data from DVP 28 is fed to the threshold value introducing device 32 which, for convenience, is called a threshold-entry device. The output of comparator 30 is generated when the intensity of the pixel composing the resultant difference image provided from DVP 28 exceeds the threshold level TH, and is a code word, such as a numeral "1", which is stored in the frame memory 34 with the address corresponding to the pixel. The code word corresponding to when the pixel data exceeds the threshold value TH in the frame memory must be coordinated or synchronized with the difference image frame to which it relates.

The counter 40 is initiated by the DVP 28 in synchronism with the pixel digital signal for the first difference image which is provided to the comparator 30, and counts the time period until the intensity of the pixel exceeds the threshold value TH. The value corresponding to the counted time period from the first difference image until when the intensity of the pixel first exceeds the threshold value TH, along with the address of the respective pixel, is stored in the imaging memory 38. The imaging memory 38 has an initializing function to keep the previously stored pixel data from counter 40 unless it is recognized that the pixel image data exceeds another threshold value TH which is reset in the threshold-entry device 32.

The phase imaging data representative of the time period stored in the imaging memory 38 is fed to a digital-to-analog converter (not shown in FIG. 1). The analog video output signals from this digital-to-analog converter are supplied to a display device 42 for displaying the mapping of time at which the concentration of contrast medium reaches the predetermined threshold value in each pixel of the blood vessels or region of interest after the contrast medium is injected, such as shown in FIG. 2.

Figure 6:
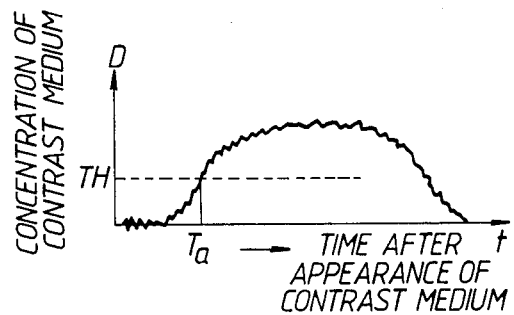
FIGS. 6, 7 and 8 are graphs showing variations in intensities of a selected picture element of interest in a sequence of subtracted images from pixel to pixel.
Figure 7:
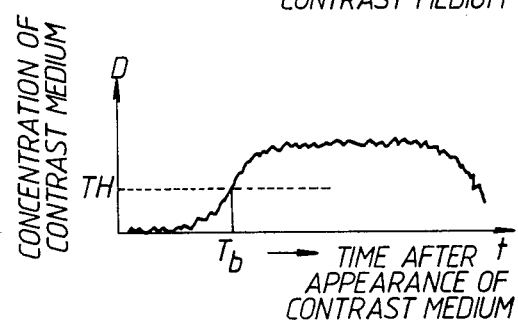
Figure 8:
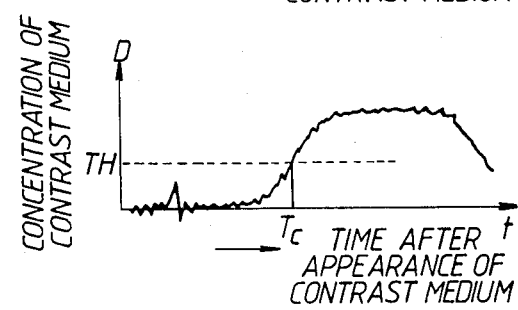

Before discussing the operating theory of the system according to the present invention, illustrative contrast medium concentrations versus time plots are repeated in FIGS. 6-8. These are really the concentrations that are represented in the projected X-ray images. It is noted that the shapes of the contrast medium concentration versus time as in FIGS. 6-8 differ, depending on which blood vessels are involved and upon where the contrast medium is injected intravenously. In particular, the shape of contrast medium concentration versus time is much affected by lesions that may exisit in the blood vessels.

Considering the nature of the concentration of contrast medium versus time, and meeting the conditions for the threshold value TH as described above, an appropriate threshold level is set in threshold entry device 32. Once the threshold value TH has been determined and set, the next step is to perform temporal subtraction.

A pre-contrast mask image is obtained and one or more successive post-contrast images are obtained. The mask is subtracted from a post-contrast image to produce an image in which everything is substantially cancelled except the image of the contrast medium. In an imaging sequence, the X-ray beam is projected continuously beginning a short time before the first mask image is obtained and remains on for a sequence of 50 or even more television image frames corresponding to X-ray images acquired over the pre-contrast period, at least the post-contrast period and possibly after the post-contrast period. In any case, the television camera 24 converts the image to corresponding analog video signals which are conducted to ADC 26. ADC 26 samples the analog video waveform and converts it to a succession of digital numbers whose values correspond to the intensities of the picture elements (pixels) that compose the image. These values are conducted to DVP 28 wherein the digital data representative of the mask image, which is the first image obtained in a sequence, is stored in a memory of DVP 28. All subsequent live pre-contrast and post-contrast images in the sequence then have the mask image value subtracted from them in succession to produce a series of difference images.

The digital data representative of the difference images are output from DVP 28 and are input to the comparator 30 wherein the digital pixel signals, i.e. the data representative of the difference images, are compared with the threshold value TH supplied from threshold-entry device 32. When the intensity of the digital pixel signal first exceeds the threshold value TH after acquisition of successive X-ray images, the imaging memory 38 is enabled to receive from the counter 40 the time signal representative of the time period between the first image in the imaging sequence until the individual pixel signal first exceeds the threshold value TH and to write the time signal into the picture element coordinated with digital difference image frame output from DVP 28. This is achieved with memory controller 36. In other words, memory controller 36, to which the output of comparator 30 is supplied, accesses the frame memory 34 to recognize whether the numeral "1" is written into the corresponding pixel in the frame memory 34, which indicates that the digital pixel signal has already exceeded the threshold value TH. If not, and the output of comparator 30 is conducted to memory controller 36, memory controller 36 functions to cause the imaging memory 38 to write in the time signals from counter 40.

The imaging memory 38 constructs a distribution of the contrast medium in the blood vessels in relation to the time periods it takes for the various pixels to attain the intensity established by the threshold value TH, which is related to the time variation of the concentration of contrast medium.

Figure 4:
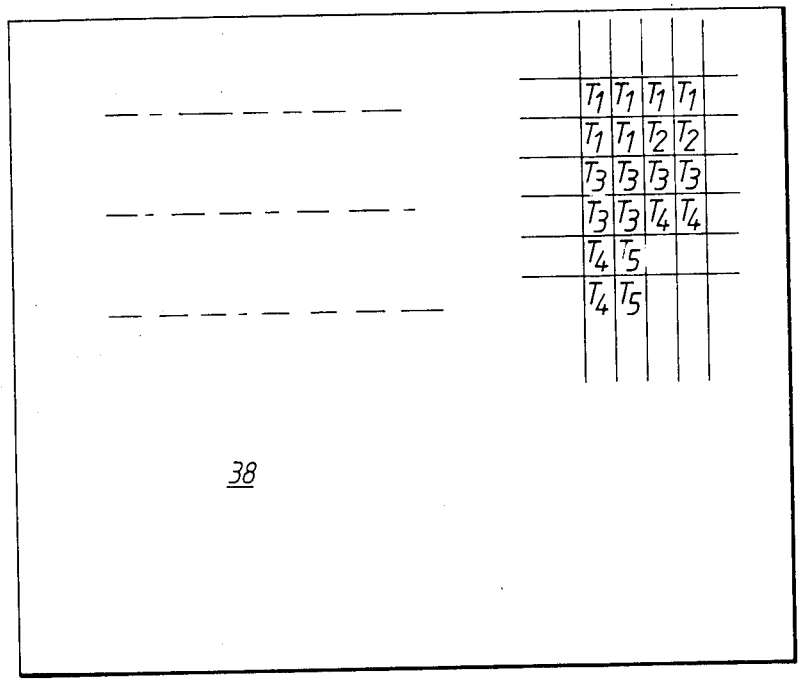
FIG. 4 is an illustration of the resultant time data stored in imaging memory 38 for each pixel obtained according to the invention as a result of comparisons of the intensity data corresponding to each pixel with a predetermined threshold voltage over successive video image frames.
Figure 3:
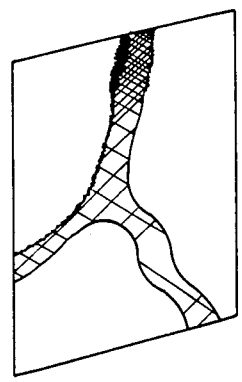
FIG. 3 is an illustration of the manner in which the subtracted images defining the outline of blood vessels may be superimposed with the contrast medium concentration or projected intensity of contrast medium in a blood vessel versus time according to the present invention.
Figure 5:
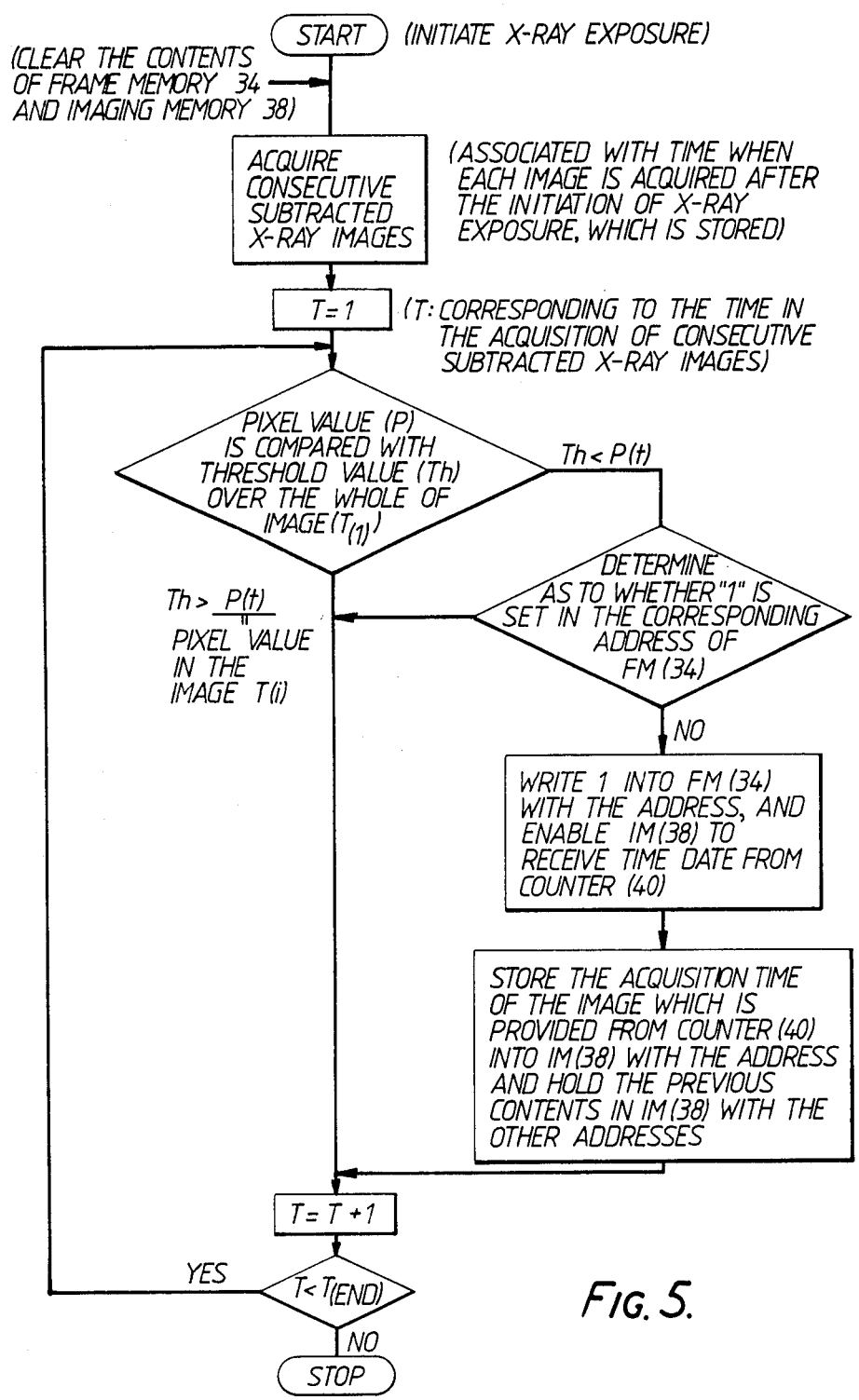
FIG. 5 is a flow chart illustrating operation of the present invention.

The same operation is performed on a succession of the difference images. Thereafter the image as shown in FIG. 3 can be constructed on the display device 42 which displays the distribution of contrast medium in the blood vessels represented by the contrast image of which each pixel has the particular magnitude proportional to the value of the time signal output from counter 40 as shown for example in FIG. 4. For example, a dark portion in the contrast image represents that the contrast medium reaches the threshold value TH rapidly in the corresponding region of blood vessels. On the contrary, a gray portion in the contrast image represents that the contrast medium reaches the threshold value TH less rapidly. As understood from the contrast image shown in FIG. 3, it is helpful for diagnosticians to inspect the phase image as shown in FIG. 3 which enables to examine not only the outline of blood vessels, but also lesions that may exist in the blood vessels. FIG. 5 is a flow chart illustrating the above described operation of the invention.

The FIG. 1 embodiment has another operating mode which is the integration mode.

Figure 9:
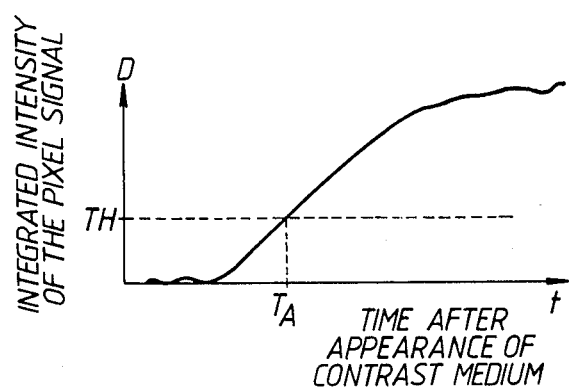
FIGS. 9-11 are graphs showing variations in intensities of an integrated pixel signal in a sequence of subtracted images from pixel to pixel, these figures being used to explain one way in which integrated data for each pixel can be compared with a predetermined reference value in an alternative processing function mode of operation or embodiment in accordance with the invention.
Figure 10:
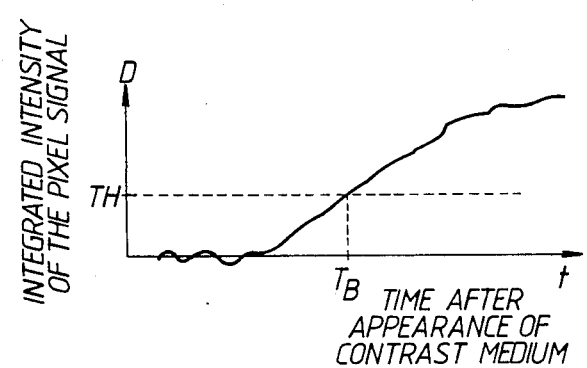
Figure 11:
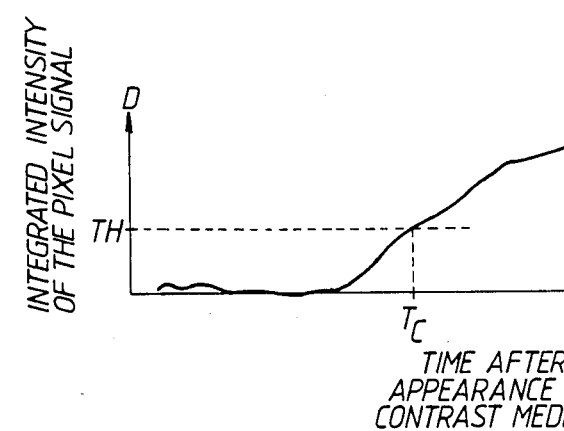

For operating in the integration mode, the digital pixel data for a plurality of difference image frames are delivered to one memory constituting DVP 28. When a predetermined number of frames are integrated in the memory, the integrated digital frame data from the memory are read out and sent to comparator 30. The plot of integrated intensity of the respective pixel signal composing the integrated difference images vs time is depicted in FIGS. 9-11. In comparator 30, the integrated pixel image signal is compared with the threshold value TH, and if the pixel data exceeds the threshold value, the comparator 30, memory controller 36, frame memory 34 and imaging memory 38 function in a fashion similar to that described above. By integrating the pixel signal over a succession of difference images the noise present in the difference image can be reduced, which enables comparator 30 to recognize with accuracy that the integrated pixel data exceeds the threshold value TH.

Further, the distribution of contrast medium in relation to the time variation for each pixel to attain an intensity defined by threshold value TH can be displayed on the screen of display device 42 in color by using a predetermined translation table to convert the pixel time difference signal to a corresponding analog video color signal.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A method for producing video signals representing phase difference images from X-ray images of a subject, which phase difference images are produced during a time period in which a contrast medium is flowing in the vessel of the subject, after intravenous injection of the contrast medium in the subject, comprising:
   acquiring a sequence of X-ray images in the form of video signals starting at the beginning of a pre-contrast period and continuing through a post-contrast period;
   producing difference video signals by performing a subtraction between the video signals of the pre-contrast images and the video signals of the post-contrast images;
   converting the difference video signals to pixel image data representative of the intensity of contrast medium at the respective pixels in the difference video signals;
   comparing the value of the pixel image data of the difference image with a predetermined threshold intensity value;
   determining, for each pixel, time data related to the time period until the intensity of the respective pixel image data reaches the predetermined threshold intensity value after acquiring a sequence of X-ray images; and
   converting said time data for each pixel into visible televison images representing the distribution of contrast medium in the vessel in relation to the time period it takes for each pixel to attain said predetermined threshold intensity value.

2. A method according to claim 1, wherein said step of converting the difference video signals to pixel image data comprises:
   integrating the pixel image data of each pixel over a predetermined number of frames of said difference video signals to produce integrated pixel image data to be compared in said comparing step.

3. A diagnostic subtraction fluorographic apparatus, comprising: an X-ray generating source for emitting radiation X-ray images of a contrast medium flowing in the vessel of a subject after intravenous injection of contrast medium into the subject;
   television means including a television camera for converting said X-ray images into a series of television video signals;
   subtracting means for producing difference video signals by performing a subtraction between the video signals of pre-contrast images and the video signals of post-contrast images, including a memory for storing said difference video signals;
   video processing means for converting said difference video signals, for each pixel, to pixel image data representative of the intensity of the contrast medium at the respective pixel in the difference video signals;
   comparator means for comparing said pixel image data with a predetermined threshold intensity value, and providing an output signal, for each pixel, when the value of the pixel image data first exceeds said threshold intensity value;
   time counting means responsive to said output of said comparator means for providing time data, for each pixel, related to time period until the intensity of the respective pixel image data reaches the predetermined threshold intensity value after acquiring a sequence of X-ray images; and
   means including a television display device for converting said time data from said time counting means into visible television images representing the distribution of contrast medium in the vessel in relation to the time period it takes for each pixel to attain said predetermined threshold intensity value.

4. An apparatus according to claim 3, wherein said video processing means comprises:
   means for integrating, for each pixel, the pixel image data of the respective pixel over a predetermined number of frames of said difference video signals to produce integrated pixel image data to be compared by said comparator means.

* * * * *